(12) United States Patent
Wassenaar et al.

(10) Patent No.: US 7,448,385 B2
(45) Date of Patent: Nov. 11, 2008

(54) NASAL ADAPTATION OF AN ORAL INHALER DEVICE

(75) Inventors: Willem Wassenaar, Ontario (CA); Alex Sochaniwskyj, Ontario (CA)

(73) Assignee: Purepharm Inc., Toronto (CA)

( * ) Notice: Subject to any disclaimer, the term of this patent is extended or adjusted under 35 U.S.C. 154(b) by 726 days.

(21) Appl. No.: 10/861,502

(22) Filed: Jun. 7, 2004

(65) Prior Publication Data
US 2005/0268915 A1    Dec. 8, 2005

(51) Int. Cl.
*A61M 11/00* (2006.01)
(52) U.S. Cl. .......................... 128/206.11; 128/200.23; 128/204.12; 128/207.18
(58) Field of Classification Search .......... 128/206.11, 128/200.14, 200.23, 204.12, 207.18
See application file for complete search history.

(56) References Cited
U.S. PATENT DOCUMENTS
2,860,634 A * 11/1958 Duncan et al. ......... 128/205.24
5,954,047 A * 9/1999 Armer et al. ........... 128/200.23
6,257,231 B1 * 7/2001 Shick et al. ............. 128/200.14
6,273,084 B1 * 8/2001 Frid ....................... 128/200.23
6,510,847 B1 * 1/2003 Helgesson et al. ...... 128/200.23

* cited by examiner

*Primary Examiner*—Steven O Douglas
(74) *Attorney, Agent, or Firm*—Clark & Brody (57) ABSTRACT

This invention is for nasal adaptors for oral inhaler devices and methods of adapting an oral inhaler device with a nasal adaptor. The nasal adaptor of the present invention, in assembly with an oral metered dose aerosol inhaler converts an oral inhaler device to nasal delivery. The nasal adaptor in assembly with an oral inhaler device when in operation, simultaneously administers an inhalant to the nasal mucosa and down to the bronchial tree and lungs. In this manner a nasally delivered anti-inflammatory agent would travel down the same route as an allergen would—the nostril, nasal cavity, nasopharynx, trachea, bronchi and lung tissues.

14 Claims, 9 Drawing Sheets

NASAL ADAPTATION OF AN ORAL INHALER DEVICE

FIELD OF THE INVENTION

The present invention relates generally to the adaptation for nasal delivery of an oral inhaler device, and more particularly to a method of adapting for nasal delivery a metered dose oral aerosol inhaler device, and a nasal adaptor for an oral metered dose aerosol inhaler device.

BACKGROUND OF THE INVENTION

One method of delivering medication is by a metered dose aerosol inhaler device and such devices may be made to provide oral or nasal delivery. Early inhalers are described in U.S. Pat. Nos. 3,361,306; 3,183,907; 3,565,070; 4,206,758; 4,803,978; 4,934,358; 4,955,371; 5,060,643; 5,351,683; 5,062,423.

An example of a typical metered dose inhaler is described herein. A pressurized dispensing canister is filled under pressure with a drug dissolved in a liquefied propellant, or micronized particles suspended in a liquefied propellant. Surfactants may be dissolved in the aerosol formulation as well. The canister is fitted with a metering valve that is movable from an inactive to an active (depressed dispensing) position. The canister containing medication is placed in the upper arm of an elbow shaped housing with the metered dose dispensing valve in position to deliver medicament through the lower arm portion and into a patient's mouth or nose, when the canister and thereby the dispensing valve is depressed against the housing. The lower arm of the housing may be configured to aid in delivery of the medication orally or nasally.

Metered dose inhalers are an accepted means for delivering medications, such as, bronchodilators, corticosteroids, and anti-allergics, in small doses to the respiratory tract. Metered dose inhalers may be a route for delivery of many other medications.

However, if nasal delivery is the desirable mode and only an oral inhaler is available, a satisfactory result may not be achieved. After the discontinuance of the use of chlorofluorocarbons (CFC's), the new non-CFC aerosol inhalers were not necessarily available with nasal delivery adaptation.

Although the same medicine may be prescribed for oral and nasal delivery, for example, beclomethasone dipropionate, the mode of delivery may need to be different to achieve the best treatment. In the past aerosol inhalers were sold to deliver this drug to the nasal mucosa for treatment of allergic rhinitis. Oral configurations of metered-dose aerosols are usually of a shape and size that is not conducive to insertion into the nostril of a human or animal.

In addition, there are side effects from oral delivery of corticosteroids that could be avoided through nasal delivery. The treatment of asthma and other lung conditions with oral inhalation steroids is associated with fungal growth in the oral cavity. This is likely due to the deposition of corticosteroids in the oral cavity. Patient instructions on the use of oral inhalation aerosols recommend that the patient rinse their mouth to remove oral corticosteroids in an attempt to reduce the incidence of candidiasis. The delivery of corticosteroids for inhalation through the nose bypasses the oral cavity and thus reduces the incidence of oral candidiasis.

The simultaneous treatment of rhinitis and asthma by delivery of a steroid through the nose rather than delivering the steroid to the lungs via the mouth and the nose locally was described in W. Pedersen, I. Hjuler, H. Bisgaard, N. Mygind, Allergy, April 1998, 53(4):383-7. Pedersen et al. found that nasal inhalation of a corticosteroid from a spacer offers a simple and effective treatment for both rhinitis and asthma. Since particles from the air, such as allergens, are deposited primarily in the nasal cavities, allergic inflammation would occur in the entire airway mucosa. Pedersen et al. used a spacer to deliver medication to the nasal mucosa. In their experiment a pressurized aerosol was attached to a spacer device and the steroid was inhaled through the nose from the spacer device. The use of a spacer, they believed, provided a more uniform intranasal drug distribution, since only inhaled air delivered the drug.

There are a number of patents that deal with the difficulty in timing the inhalation of breath with the depression of the dispensing valve—U.S. Pat. Nos. 6,615,826; 4,972,830; 5,758,638. There are other patents that deal with the adaptation of an inhaler for nasal delivery with a mask, particularly for animals, for instance, U.S. Pat. Nos. 6,510,818 and 5,666, 948. However, a drawback of a spacer or mask is the decreased dose of medication due to the increased distance to the nasal cavity, and increased surface on which the medication may adhere. To avoid this problem by increasing the amount of medication dispensed is uneconomical.

Aqueous nasal sprays delivered by pump action are an alternative to aerosol inhalers. However, with aqueous delivery, a set concentration is delivered to the mucosa since subsequent sprays result in the extra aqueous solution being swallowed. In contrast, a metered dose aerosol delivery allows a greater concentration of inhalant to be delivered to the nasal mucosa. Since the propellant is a vapour that dissipates, subsequent doses result in extra medication being deposited on the nasal mucosa.

Therefore it would be desirable to provide a method of adapting an oral metered dose aerosol inhaler and also to provide an adaptor for an oral metered dose aerosol inhaler to enable effective nasal delivery.

SUMMARY OF THE INVENTION

This invention is for nasal adaptors for oral inhaler devices and methods of adapting an oral inhaler device with a nasal adaptor. The oral inhaler device comprises a housing and a canister containing inhalant. The housing comprises an upper arm and a lower arm.

In a first embodiment of the invention a nasal adaptor has a first end and a second end, such that when said nasal adaptor is assembled with an oral inhaler device said second end is available for insertion in a nostril. Furthermore said first end and said second end are the ends of a tube, and said first end has a circumference that is the same as or greater than said second end.

In one adaptation, the nasal adaptor may also comprise longitudinal flanges between said first end and said second end to provide a snug fit when assembled, such that said longitudinal flanges do not interfere with the insertion of said second end in a nostril. The longitudinal flanges may include protuberances that abut the open end of said lower arm of said housing when assembled. In addition, the nasal adaptor may also comprise a circular flange at substantially the first end of said nasal adaptor.

In an alternate adaptation, the nasal adaptor has a circular flange positioned between said first end and second end. This circular flange may be contiguous with a rim which fits snugly over the lower arm of said housing when assembled.

In a second embodiment of the invention, a nasal adaptor for an oral inhaler device, comprises a sleeve and a hollow cylinder at the base of said sleeve, such that when said nasal adaptor is assembled with a modified version of an oral inhaler device said cylinder is available for insertion in a nostril.

The modification of the oral inhaler device is to the housing, wherein said lower arm is capable of detachment at a point along the lower arm, and said lower arm is detached when said nasal adaptor is assembled with said oral inhaler device.

In a third embodiment of the invention, a nasal adaptor for an oral inhaler device, has a first end and a second end, such that when said nasal adaptor is assembled with a modified version of an oral inhaler device the second end of said nasal adaptor is available for insertion in a nostril. The modification of the oral inhaler device is to the housing, wherein said lower arm is capable of detachment at a point along the lower arm, and said lower arm is detached when said nasal adaptor is assembled with said oral inhaler device. The nasal adaptor's first end and second end are the ends of a tube, and said first end has a circumference that is the same as or greater than said second end. The nasal adaptor has a circular flange positioned between said first end and second end. The circular flange may be contiguous with a rim at right angles projecting towards the first end, which fits snugly over the remainder of the lower arm of said housing and is partially carved out to abut the upper arm of said housing, when in assembly.

A further embodiment of the invention is the method of assembling a nasal adaptor with an oral inhaler device comprised of a housing and canister containing inhalant, said housing having an upper arm and a lower arm, by inserting the first end of said nasal adaptor into the lower arm of said housing.

A further embodiment of the invention is the method of assembling a nasal adaptor with an oral inhaler device comprised of a housing and canister containing inhalant, said housing having an upper arm and a lower arm, which lower arm is capable of detachment at a point along the lower arm, by detaching the lower arm and pushing the upper arm into said sleeve so that said cylinder is in the spatial position formerly occupied by said lower arm.

A further embodiment of the invention is the method of assembling a nasal adaptor with an oral inhaler device comprised of a housing and canister containing inhalant, said housing having an upper arm and a lower arm, which lower arm is capable of detachment at a point along the lower arm, by detaching the lower arm and inserting the first end of said nasal adaptor into the remaining lower arm of said housing.

A further embodiment is a kit comprising a nasal adaptor and one of either:
  a. an oral inhaler device;
  b. a housing for holding a canister containing inhalant;
  c. a canister containing inhalant; or
  d. a housing in which the lower arm may be detached.

DETAILED DESCRIPTION OF THE PREFERRED EMBODIMENTS

Normally persons at rest breathe through the nose, the natural entrance to the mammalian airways. Allergens and irritants in the air are largely deposited in the nasal cavities and to a lesser degree, in the bronchi. Allergic inflammation in the entire airway mucosa would be expected in allergy sufferers, whether the predominant symptom is rhinitis, asthma or both.

Since rhinitis and asthma often occur together, the standard treatment of allergic rhinitis and asthma consists of topical anti-inflammatory administered intra-nasally and inhaled through the mouth. However, nasal delivery alone is a preferred method to deliver medication to the site of inflammation and avoid side effects such as oral candidiasis.

The nasal adaptor of the present invention, fitted to the lower arm of an oral metered dose aerosol inhaler provides the means to simultaneously administer drug to the nasal mucosa and down to the bronchial tree and lungs. In this manner a nasally delivered anti-inflammatory agent would travel down the same route as an allergen would—the nostril, nasal cavity, nasopharynx, trachea, bronchi and lung tissues.

The nasal adaptor may be modified to fit oral inhaler devices of various shapes and sizes. The canister can be filled with an inhalant that is suitable for nasal delivery. Such inhalant may be anything capable of improving health, preventing disease and treating conditions, such as medicines, vaccines, chemotherapeutics etc. The nasal adaptor may replace or be added to the lower arm of the oral dispensing device housing. As such, the nasal adaptor may be inserted in or fitted over the lower arm of the housing, or be added to the housing after the lower arm is modified by removal of the whole or a portion.

The nasal adaptor provides a smaller circumference than the orally adapted lower arm of the housing at the point of entry into the nostril. The nasal adaptor is most effective if it is designed to minimize the amount of inhalant lost, and to minimize any inhalant lost due to the presence of the nasal adaptor. The most desired nasal adaptor is designed to direct flow of the medication into the nostril.

Figure 1:
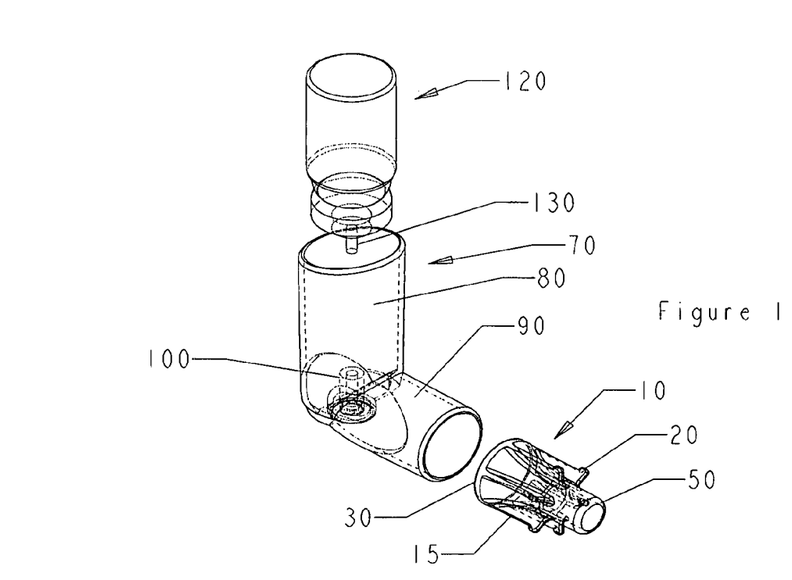
FIG. 1 is an exploded perspective view of an oral metered dose inhaler device and nasal adaptor of embodiment 1 of the invention.

FIG. 1 is an exploded perspective view of an oral metered dose inhaler device and nasal adaptor of embodiment 1 of the invention. The oral metered dose inhaler device is comprised of an elbow shaped housing and a canister containing the inhalant to be delivered. The nasal adaptor 10 is sized to fit snugly within lower arm 90 of housing 70 when in assembly. The nasal adaptor 10 is fitted with flanges 15 that assist in providing a snug fit and the protuberances 20 on each flange secure the position of the nasal adaptor in lower arm 90 of the housing 70 when in assembly. The nasal adaptor 10 has a first end 30 and a second end 50. The first end 30 of the nasal adaptor 10 of embodiment 1 is sized to fit snugly within the circumference of the lower arm 90 of the housing 70, and taper to the second end 50 sized to fit in a nostril. The housing 70 is elbow shaped and the upper arm 80 is contiguous with lower arm 90. The housing 70 is shown with a cutaway to expose the valve housing 100 at the base of the upper arm 80. The canister 120 has a dispensing valve 130.

Figure 2:
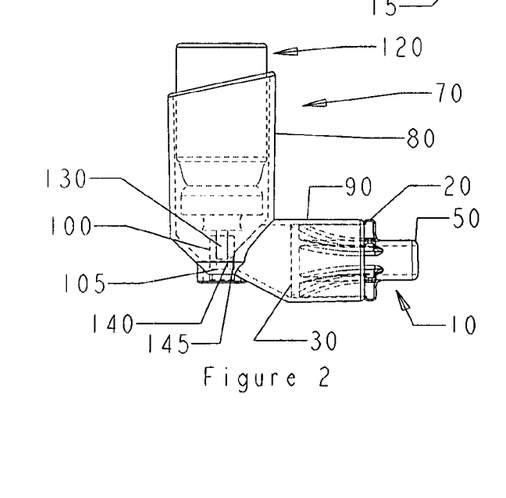
FIG. 2 is a side view of an oral metered dose inhaler device and nasal adaptor of embodiment 1, in assembly.

FIG. 2 is a side view of an oral metered dose inhaler device and nasal adaptor of embodiment 1, in assembly. The canister 120 containing an inhalant, as well as a propellant and possibly other ingredients such as surfactant, is placed in the upper arm 80 of the housing 70 so that the dispensing valve 130 rests within valve housing 100. The nasal adaptor 10 fits snugly within the lower arm 90 of the housing 70. The nasal adaptor 10 is fitted into the lower arm 90 of the housing 70 such that the protuberances 20 abut the open end of the lower arm 90. When the canister 120 is depressed into the upper arm 80 of the housing 70, the dispensing valve 130 is depressed against the floor 105 of the valve housing 100, causing the release of pressurized inhalant out of an aperture in dispensing valve 130 and through an aperture 140 in housing valve 100, which aperture 140 sits in concavity 145 in housing valve 100. The inhalant then travels through lower arm 90, through first end 30 and second end 50 in the nasal adaptor 10. In actual use, the second end 50 of the nasal adaptor would be placed in a nostril and the medication would travel out of the second end 50 in the nasal adaptor 10 and into the nostril, through the airways to the lungs, depositing the inhalant throughout.

The details of the housing such as the aperture 140 and concavity 145 are provided to demonstrate how the invention of a nasal adaptor works in this particular canister and housing environment.

Figures 3, 4:
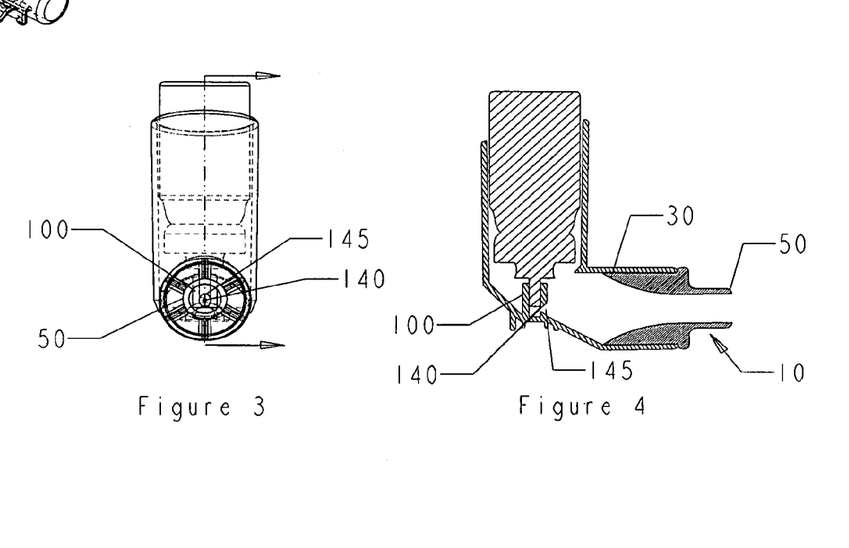
FIG. 3 is a front view of an oral metered dose inhaler device and nasal adaptor of embodiment 1, in assembly.
FIG. 4 is a cross-sectional side view of the assembly shown in FIG. 3.

FIG. 3 is a front view of a metered dose inhaler device and nasal adaptor embodiment 1, in assembly. This view demonstrates that the aperture 140 of the valve housing 100 is lined up within the circumference of the second end 50 of the nasal adaptor 10.

FIG. 4 is a cross-sectional side view sectioned along the arrows of the assembly shown in FIG. 3. This view demonstrates that the aperture 140 of the valve housing 100 is lined up within the circumference of both the first end 30 and second end 50 of the nasal adaptor 10.

Figure 5:
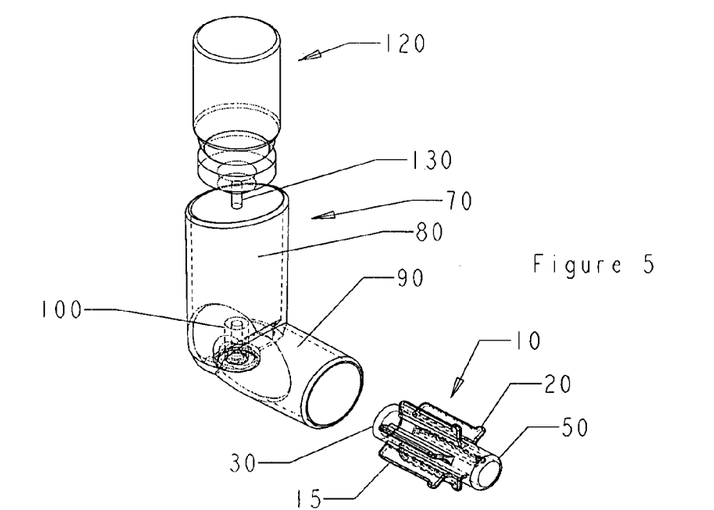
FIG. 5 is an exploded perspective view of an oral metered dose inhaler device and nasal adaptor of embodiment 2 of the invention.

FIG. 5 is an exploded perspective view of an oral metered dose inhaler device and nasal adaptor of embodiment 2 of the invention. The oral metered dose inhaler device is comprised of an elbow shaped housing and a canister containing the inhalant to be delivered. The nasal adaptor 10 is sized to fit snugly within the lower arm 90 of housing 70. The nasal adaptor 10 is fitted with flanges 15 that assist in providing a snug fit and the protuberances 20 on each flange secure its position in lower arm 90 of the housing 70. The nasal adaptor has a first end 30 and a second end 50 of approximately the same circumference. The second end 50 is sized to fit in a nostril. The housing 70 is elbow shaped and the upper arm 80 is contiguous with lower arm 90. The housing 70 is shown with a cutaway to expose the valve housing 100 at the base of the upper arm 80. The canister 120 has a dispensing valve 130.

Figure 6:
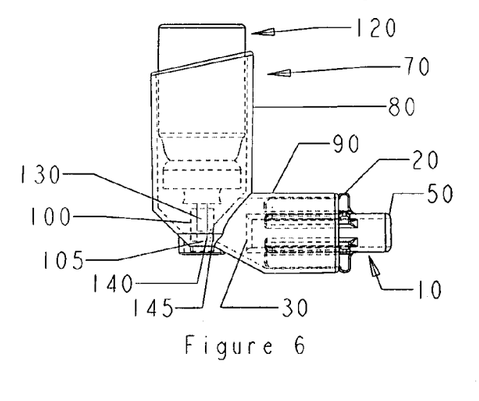
FIG. 6 is a side view of an oral metered dose inhaler device and nasal adaptor of embodiment 2, in assembly.

FIG. 6 is a side view of an oral metered dose inhaler device and nasal adaptor embodiment 2, in assembly. The canister 120 containing an inhalant, a propellant and possibly other ingredients such as surfactant, is placed in the upper arm 80 of the housing 70 so that the dispensing valve 130 fits into the valve housing 100. The nasal adaptor 10 fits snugly in the lower arm 90 of the housing 70. The nasal adaptor 10 is fitted into the lower arm 90 of the housing 70 such that the protuberances 20 abut the open end of the lower arm 90. When the canister is depressed into the upper arm 80 of the housing 70, the dispensing valve 130 is depressed against the floor 105 of the valve housing 100, causing the release of pressurized inhalant out of an opening in dispensing valve 130 and through an aperture 140 in housing valve 100, which aperture 140 sits in concavity 145 in housing valve 100. The inhalant then travels through lower arm 90, through first end 30 and second end 50 in the nasal adaptor 10. In actual use, the second end 50 of the nasal adaptor 10 would be placed in a nostril and the inhalant would travel out of the second end 50 in the nasal adaptor 10 and into the nostril, through the airways to the lungs, depositing the inhalant throughout.

Figures 7, 8:
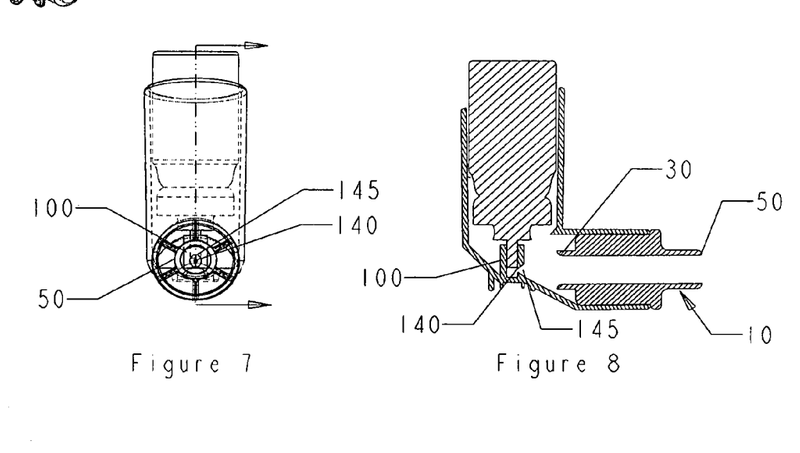
FIG. 7 is a front view of an oral metered dose inhaler device and nasal adaptor of embodiment 2, in assembly.
FIG. 8 is a cross-sectional side view of the assembly shown in FIG. 7.

FIG. 7 is a front view of an oral metered dose inhaler device and nasal adaptor embodiment 2, in assembly. This view demonstrates that the aperture 140 of the valve housing 100 is lined up within the circumference of the second end 50 of the nasal adaptor 10.

FIG. 8 is a cross-sectional side view sectioned along the arrows of the assembly shown in FIG. 7. This view demonstrates the positioning of the aperture 140 of the valve housing 100 within the circumference of first end 30 and second end 50 of the nasal adaptor 10.

Figure 9:
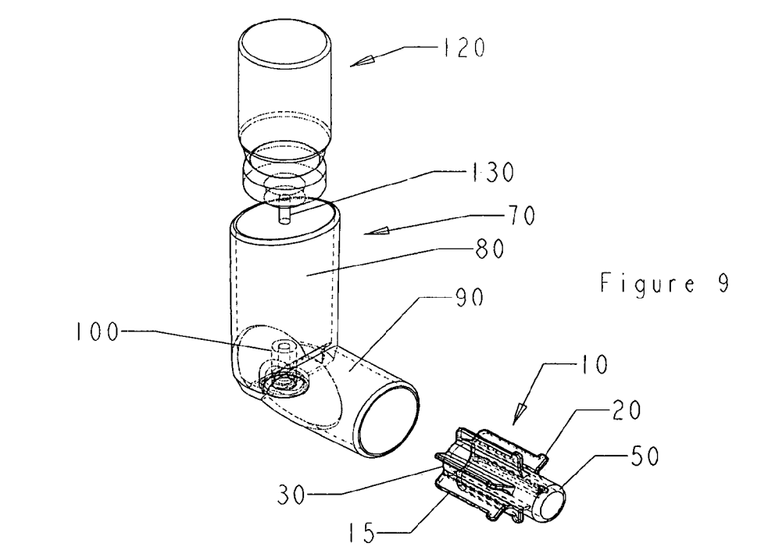
FIG. 9 is an exploded perspective view of an oral metered dose inhaler device and nasal adaptor of embodiment 3 of the invention.

FIG. 9 is an exploded perspective view of an oral metered dose inhaler device and nasal adaptor of embodiment 3 of the invention. The oral metered dose inhaler device is comprised of an elbow shaped housing and a canister containing the inhalant to be delivered. The nasal adaptor 10 is sized to fit snugly within the lower arm 90 of housing 70. The nasal adaptor 10 is fitted with flanges 15 that assist in providing a snug fit and the protuberances 20 on each flange secure its position in lower arm 90 of the housing 70. The nasal adaptor has a first end 30 and a second end 50 of approximately the same circumference. The first end 30 is flush with the first end of the flanges. The second end 50 is sized to fit in a nostril. The housing 70 is elbow shaped and the upper arm 80 is contiguous with lower arm 90. The housing 70 is shown with a cutaway to expose the valve housing 100 at the base of the upper arm 80. The canister 120 has a dispensing valve 130.

Figure 10:
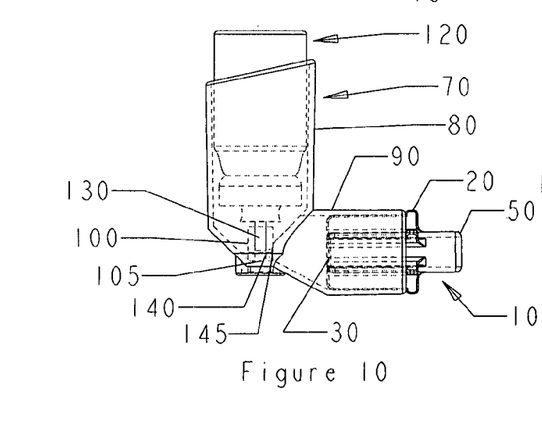
FIG. 10 is a side view of an oral metered dose inhaler device and nasal adaptor of embodiment 3, in assembly.

FIG. 10 is a side view of an oral metered dose inhaler device and nasal adaptor embodiment 3, in assembly. The canister 120 containing an inhalant, a propellant and possibly other ingredients such as surfactant, is placed in the upper arm 80 of the housing 70 so that the dispensing valve 130 fits into the valve housing 100. The nasal adaptor 10 fits snugly in the lower arm 90 of the housing 70. The nasal adaptor 10 is fitted into the lower arm 90 of the housing 70 such that the protuberances 20 abut the open end of the lower arm 90. When the canister is depressed into the upper arm 80 of the housing 70, the dispensing valve 130 is depressed against the floor 105 of the valve housing 100, causing the release of pressurized inhalant out of an opening in dispensing valve 130 and through an aperture 140 in housing valve 100, which aperture 140 sits in concavity 145 in housing valve 100. The inhalant then travels through lower arm 90, through first end 30 and second end 50 in the nasal adaptor 10. In actual use, the second end 50 of the nasal adaptor 10 would be placed in a nostril and the inhalant would travel out of the second end 50 in the nasal adaptor 10 and into the nostril, through the airways to the lungs, depositing the inhalant throughout.

Figures 11, 12:
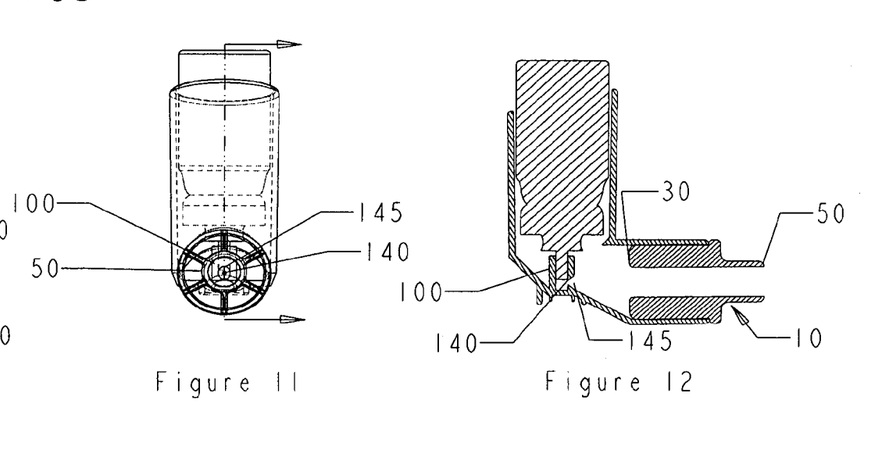
FIG. 11 is a front view of an oral metered dose inhaler device and nasal adaptor of embodiment 3, in assembly.
FIG. 12 is a cross-sectional side view of the assembly shown in FIG. 11.

FIG. 11 is a front view of a metered dose inhaler device and nasal adaptor embodiment 3, in assembly. This view demonstrates that the aperture 140 of the valve housing 100 is lined up within the circumference of the second end 50 of the nasal adaptor 10.

FIG. 12 is a cross-sectional side view sectioned along the arrows of the assembly shown in FIG. 7. This view demonstrates the positioning of the aperture 140 of the valve housing 100 within the circumference of first end 30 and second end 50 of the nasal adaptor 10.

Figure 13:
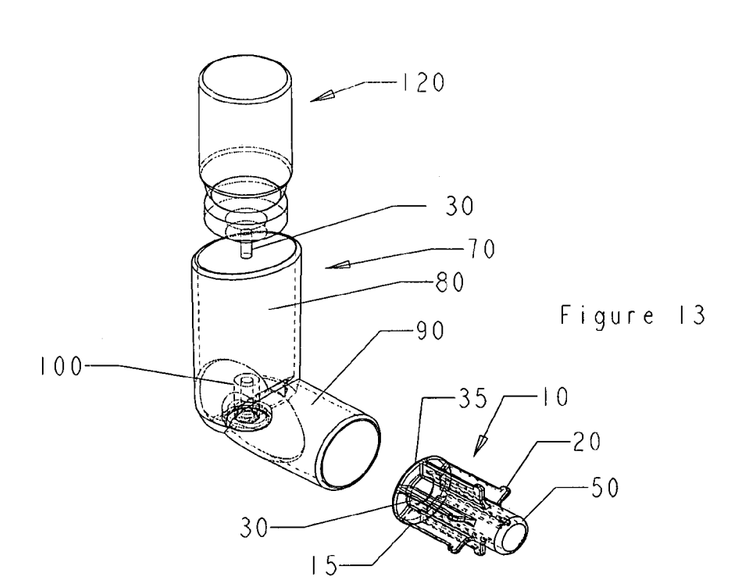
FIG. 13 is an exploded perspective view of an oral metered dose inhaler device and nasal adaptor of embodiment 4 of the invention.

FIG. 13 is an exploded perspective view of an oral metered dose inhaler device and nasal adaptor of embodiment 4 of the invention. The oral metered dose inhaler device is comprised of an elbow shaped housing 70 and a canister 120 containing the inhalant to be delivered. The nasal adaptor 10 is sized to fit snugly within the lower arm 90 of the housing 70. The nasal adaptor 10 is fitted with flanges 15 that assist in providing a snug fit and the protuberances 20 on each flange secure its position in the housing 70. The nasal adaptor 10 has an encircling flange 35 at first end 30. The nasal adaptor has a first end 30 and a second end 50 of approximately the same circumference. The second end 50 is sized to fit in a nostril. The housing 70 is elbow shaped and the upper arm 80 is contiguous with lower arm 90. The housing 70 is shown with a cutaway to expose the valve housing 100 at the base of the upper arm 80. The canister 120 has a dispensing valve 130.

Figure 14:
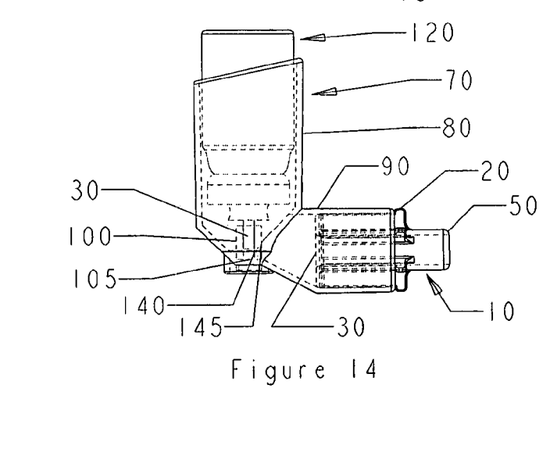
FIG. 14 is a side view of an oral metered dose inhaler device and nasal adaptor of embodiment 4, in assembly.

FIG. 14 is a side view of an oral metered dose inhaler device and nasal adaptor embodiment 4, in assembly. The canister 120 containing an inhalant, a propellant and possibly other ingredients such as surfactant, is placed in the upper arm 80 of the housing 70 so that the dispensing valve 130 fits into the valve housing 100. The nasal adaptor 10 fits snugly in the lower arm 90 of the housing 70. The nasal adaptor 10 is fitted into the lower arm 90 of the housing 70 such that the protuberances 20 abut the open end of the lower arm 90. When the canister is depressed into the upper arm 80 of the housing 70, the dispensing valve 130 is depressed against the floor 105 of the valve housing 100, causing the release of pressurized inhalant out of an opening in dispensing valve 130 and through an aperture 140 in housing valve 100, which aperture 140 sits in concavity 145 in housing valve 100. The inhalant then travels through lower arm 90, through first end 30 and second end 50 in the nasal adaptor 10. In actual use, the second end 50 of the nasal adaptor 10 would be placed in a nostril and the inhalant would travel out of the second end 50 in the nasal adaptor 10 and into the nostril, through the airways to the lungs, depositing the inhalant throughout.

Figure 15:
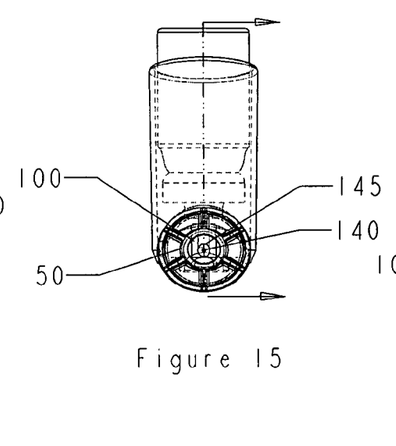
FIG. 15 is a front view of an oral metered dose inhaler device and nasal adaptor of embodiment 4, in assembly.

FIG. 15 is a front view of a metered dose inhaler housing and nasal adaptor of embodiment 4, in assembly. This view demonstrates that the aperture 140 of the valve housing 100 is lined up within the circumference of the second end 50 of the nasal adaptor 10.

Figure 16:
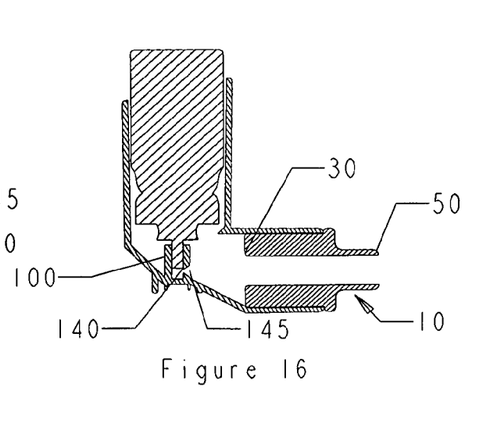
FIG. 16 is a cross-sectional side view of the assembly shown in FIG. 15.

FIG. 16 is a cross-sectional side view sectioned along the arrows of the assembly shown in FIG. 7. This view demonstrates the positioning of the aperture 140 of the valve housing 100 within the circumference of first end 30 and second end 50 of the nasal adaptor 10.

Figures 17, 18, 19:
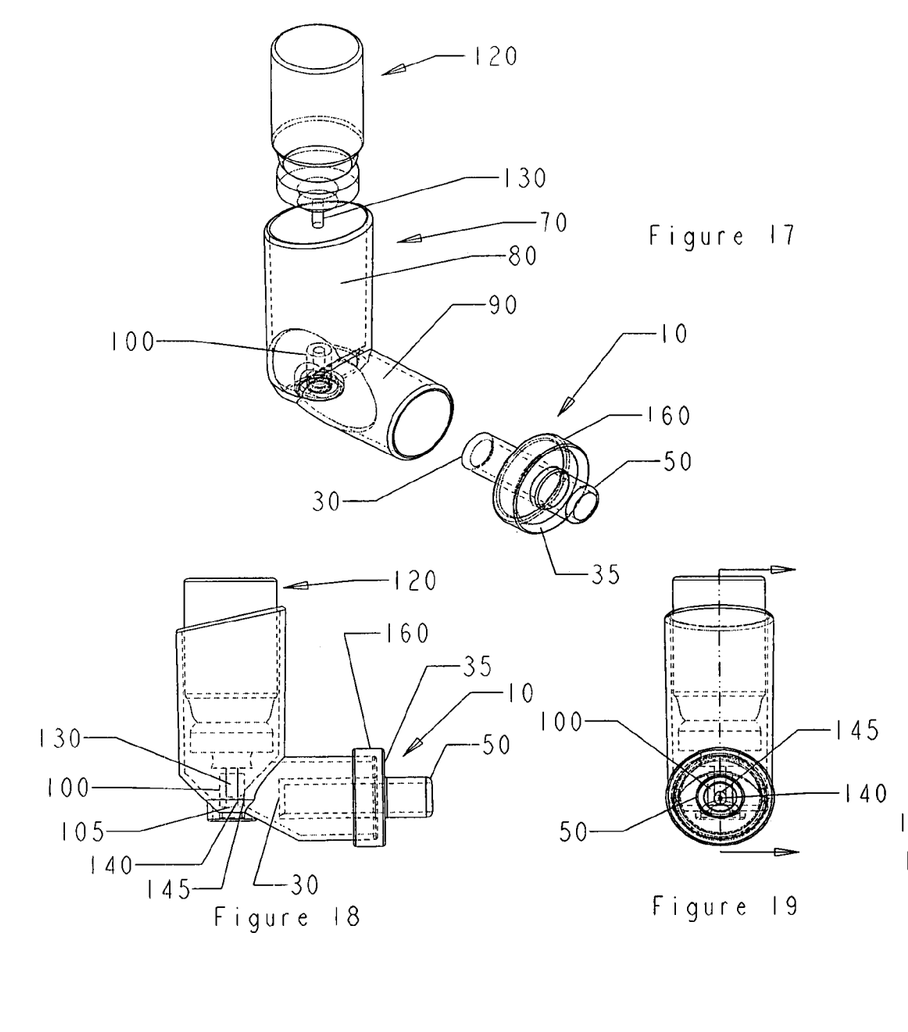
FIG. 17 is an exploded perspective view of an oral metered dose inhaler device and nasal adaptor of embodiment 5 of the invention.
FIG. 18 is a side view of an oral metered dose inhaler device and nasal adaptor of embodiment 5, in assembly.
FIG. 19 is a front view of an oral metered dose inhaler device and nasal adaptor of embodiment 5, in assembly.

FIG. 17 is an exploded perspective view of an oral metered dose inhaler device and nasal adaptor of embodiment 5 of the invention. The oral metered dose inhaler device is comprised of an elbow shaped housing and a canister containing the inhalant to be delivered. The nasal adaptor 10 is sized to fit snugly within lower arm 90 of the housing 70. The nasal adaptor has a first end 30 and a second end 50 of approximately the same circumference. The nasal adaptor 10 has an encircling flange 35, positioned between first end 30 and second end 50, that abuts the open end of the lower arm 90 when in assembly. The encircling flange 35 is contiguous with a rim 160 that fits snugly over the lower arm 90 of the housing 70, when in assembly. The second end 50 is sized to fit in a nostril. The housing 70 is elbow shaped and the upper arm 80 is contiguous with lower arm 90. The housing 70 is shown with a cutaway to expose the valve housing 100 at the base of the upper arm 80. The canister 120 has a dispensing valve 130.

FIG. 18 is a side view of an oral metered dose inhaler device and nasal adaptor embodiment 5, in assembly. The canister 120 containing an inhalant, a propellant and possibly other ingredients such as surfactant, is placed in the upper arm 80 of the housing 70 so that the dispensing valve 130 fits into the valve housing 100. The nasal adaptor 10 fits snugly with the lower arm 90 of the housing 70. The nasal adaptor 10 is fitted into the lower arm 90 of the housing 70 such that the encircling flange 35 abuts the open end of the lower arm 90. When the canister is depressed into the upper arm 80 of the housing 70, the dispensing valve 130 is depressed against the floor 105 of the valve housing 100, causing the release of pressurized inhalant out of an opening in dispensing valve 130 and through an aperture 140 in housing valve 100, which aperture 140 sits in concavity 145 in housing valve 100. The inhalant then travels through lower arm 90, through first end 30 and second end 50 in the nasal adaptor 10. In actual use, the second end 50 of the nasal adaptor 10 would be placed in a nostril and the inhalant would travel out of the second end 50 in the nasal adaptor 10 and into the nostril, through the airways to the lungs, depositing the inhalant throughout.

FIG. 19 is a front view of a metered dose inhaler device and nasal adaptor embodiment 5, in assembly. This view demonstrates that the aperture 140 of the valve housing 100 is lined up within the circumference of the second end 50 of the nasal adaptor 10.

Figure 20:
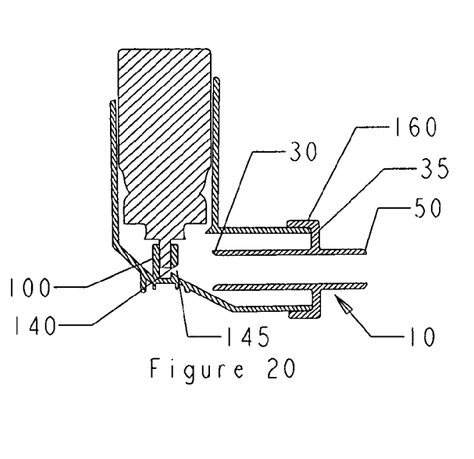
FIG. 20 is a cross-sectional side view of the assembly shown in FIG. 19.

FIG. 20 is a cross-sectional side view sectioned along the arrows of the assembly shown in FIG. 7. This view demonstrates the positioning of the aperture 140 of the valve housing 100 within the circumference of first end 30 and second end 50 of the nasal adaptor 10. It also demonstrates that the inhalant would not pass through encircling flange 35.

Figure 21:
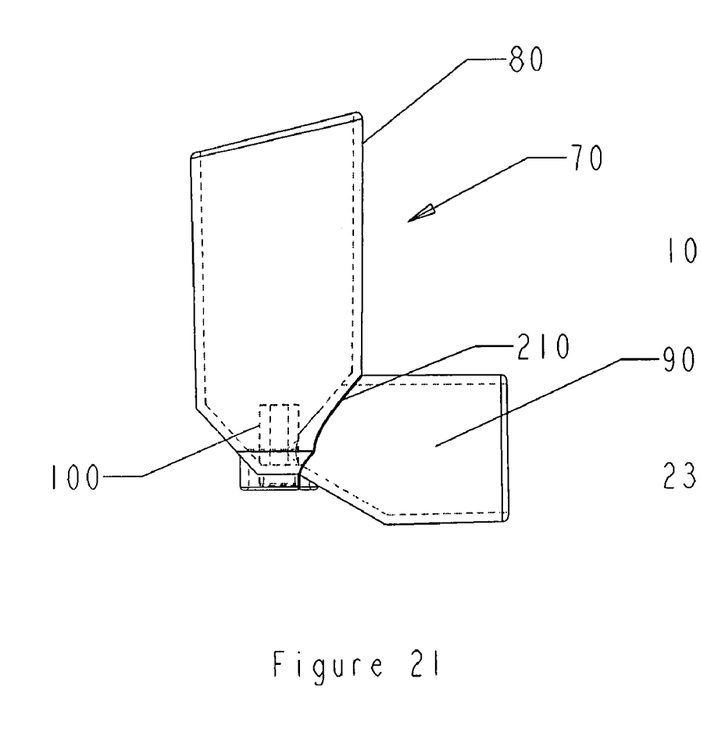
FIG. 21 is a side view of an oral metered dose inhaler housing of embodiment 6 with detachable lower arm.

FIG. 21 is a side view of an oral metered dose inhaler housing 70 of embodiment 6 with break line 210. The housing 70 is elbow shaped with upper arm 80 contiguous with lower arm 90.

Figure 22:
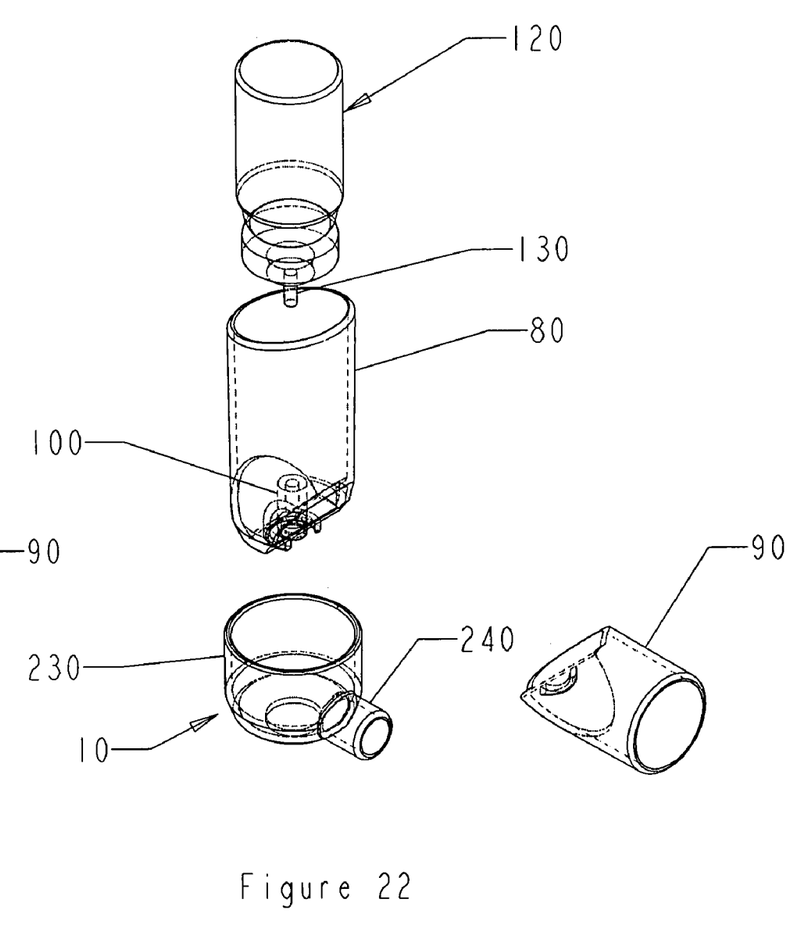
FIG. 22 is an exploded perspective view of a modified oral metered dose inhaler device and nasal adaptor of embodiment 6.

FIG. 22 is an exploded perspective view of a modified oral metered dose inhaler device and nasal adaptor of embodiment 6. The oral metered dose inhaler device is comprised of an elbow shaped housing 70 and a canister 120 containing the inhalant to be delivered. The lower arm 90 is detachable from the housing at break line 210. The housing is shown with a cutaway to expose the valve housing 100 at the base of the upper arm 80. The canister has a dispensing valve 130. The nasal adaptor 10 has a sleeve 230 from which a cylinder 240 projects.

Figure 23:
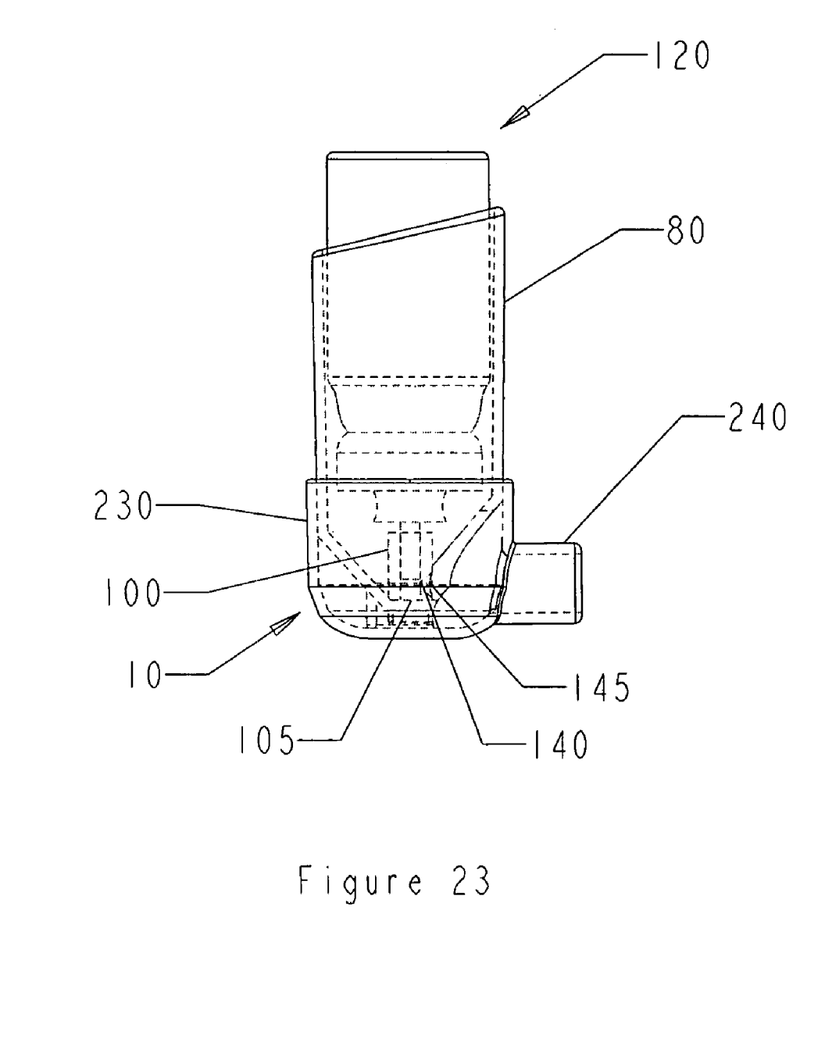
FIG. 23 is a side view of a modified oral metered dose inhaler device and nasal adaptor of embodiment 6, in assembly.

FIG. 23 is a side view of a modified oral metered dose inhaler device and nasal adaptor of embodiment 6, in assembly. The canister 120 containing an inhalant, a propellant and possibly other ingredients such as surfactant, is placed in the upper arm 80 of the housing 70 so that the dispensing valve 130 fits into the valve housing 100. The sleeve 230 of the nasal adaptor 10 fits over the lower portion of upper arm 80 and cylinder 240 is in the spatial position formerly occupied by said lower arm. When the canister is depressed into the upper arm 80 of the housing 70, the dispensing valve 130 is depressed against the floor 105 of the valve housing 100, causing the release of pressurized inhalant out of an opening in dispensing valve 130 and through an aperture 140 in housing valve 100, which aperture 140 sits in concavity 145 in housing valve 100. The inhalant then travels through cylinder 240 in the nasal adaptor 10. In actual use, the cylinder 240 would be placed in a nostril and the inhalant would travel into the nostril, through the airways to the lungs, depositing the inhalant throughout.

Figure 24:
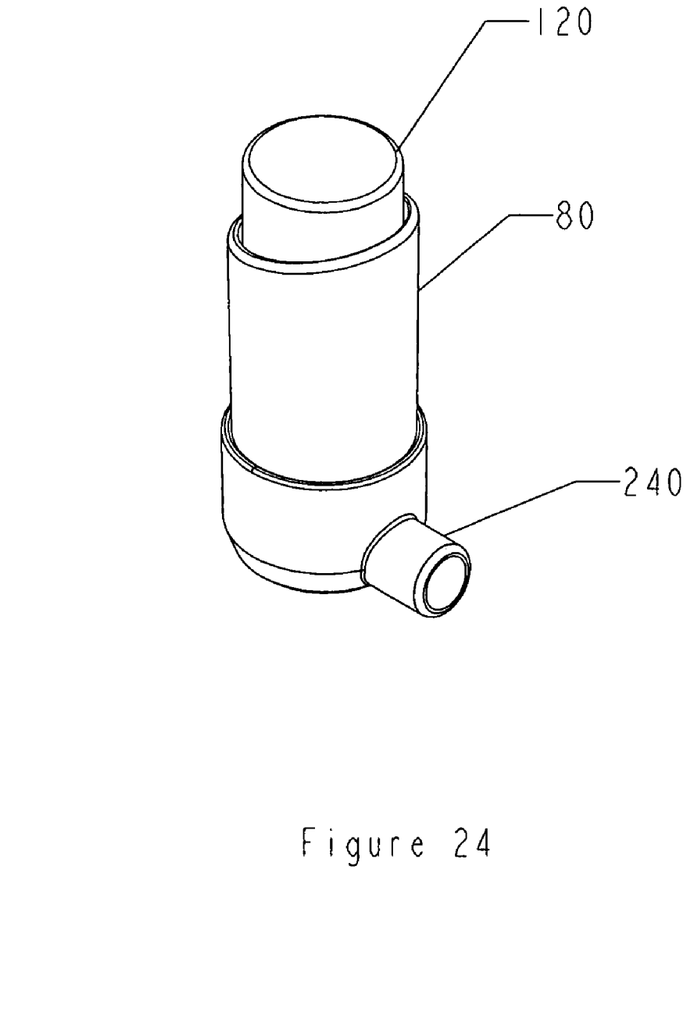
FIG. 24 is a perspective view of a modified oral metered dose inhaler device and nasal adaptor of embodiment 6, in assembly.

FIG. 24 is a perspective view of a modified oral metered dose inhaler device and nasal adaptor of embodiment 6, in assembly.

Figure 25:
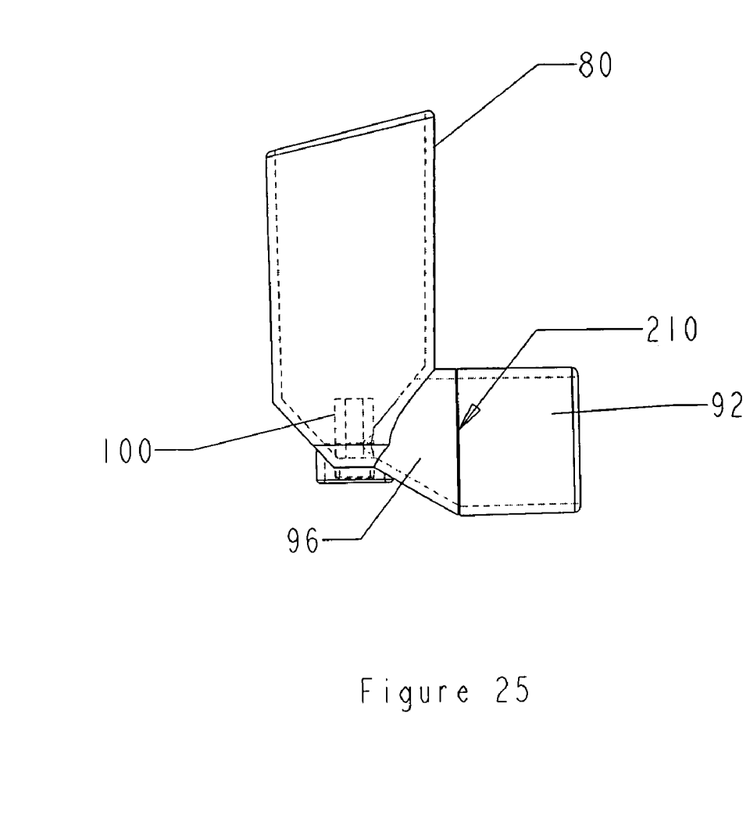
FIG. 25 is a side view of an oral metered dose inhaler housing of embodiment 6 with detachable lower arm.

FIG. 25 is a side view of an oral metered dose inhaler device housing 70 of embodiment 7 with break line 210. The housing 70 is elbow shaped with upper arm 80 contiguous with a first lower arm 96 that is contiguous with a second lower arm 92.

Figure 26:
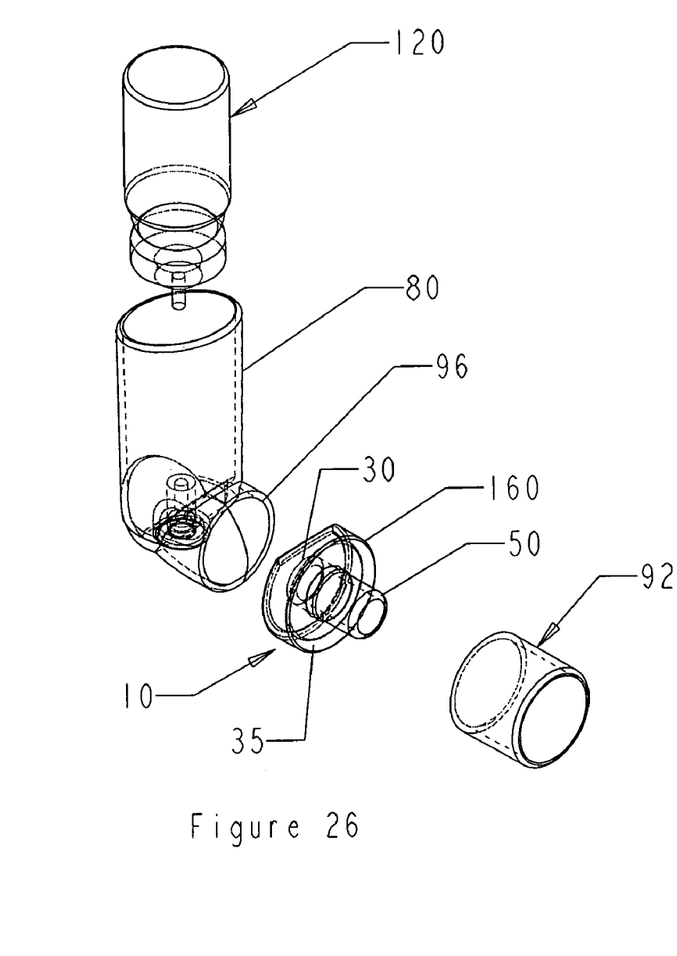
FIG. 26 is an exploded perspective view of a modified oral metered dose inhaler device and nasal adaptor of embodiment 7.

FIG. 26 is an exploded perspective view of a modified oral metered dose inhaler device and nasal adaptor of embodiment 7. The oral metered dose inhaler device is comprised of an elbow shaped housing 70 and a canister 120 containing the inhalant to be delivered. The second lower arm 92 is broken off of the housing at break line 210. The housing is shown with a cutaway to expose the valve housing 100 at the base of the upper arm 80. The canister 120 has a dispensing valve 130. The nasal adaptor 10 is sized to fit snugly within lower arm 96 of the housing 70. The nasal adaptor has a first end 30 and a second end 50 of approximately the same circumference. The nasal adaptor 10 has an encircling flange 35, positioned between first end 30 and second end 50, that abuts the open end of lower arm 96 when in assembly. The encircling flange 35 is contiguous with a rim 160 that fits snugly over the lower arm 96 of the housing 70, when in assembly. The rim 160 is indented where it meets upper arm 80 so as to fit flush against upper arm 80. The second end 50 is sized to fit in a nostril.

Figure 27:
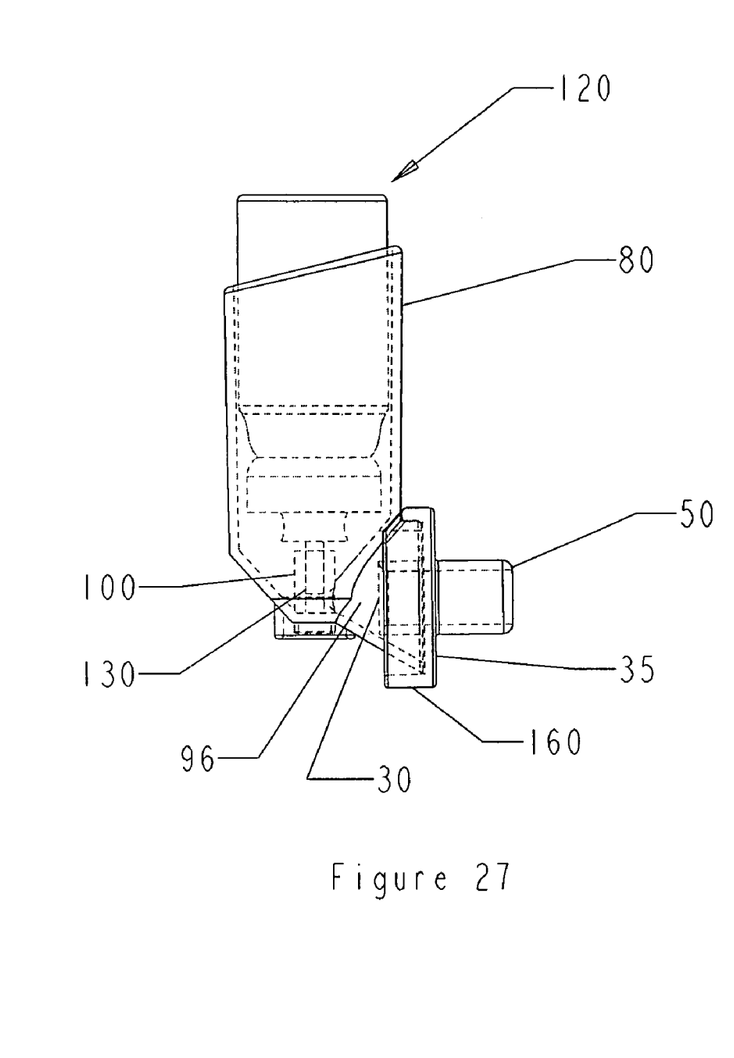
FIG. 27 is a side view of a modified oral metered dose inhaler device and nasal adaptor of embodiment 7, in assembly.

FIG. 27 is a side view of a modified oral metered dose inhaler device and nasal adaptor of embodiment 7, in assembly. The canister 120 containing an inhalant, a propellant and possibly other ingredients such as surfactant, is placed in the upper arm 80 of the housing 70 so that the dispensing valve 130 fits into the valve housing 100. The rim 160 of the nasal adaptor 10 fits over first lower arm 96 when in assembly, and encircling flange 35 abuts the open end of first lower arm 96. When the canister is depressed into the upper arm 80 of the housing 70, the dispensing valve 130 is depressed against the floor 105 of the valve housing 100, causing the release of pressurized inhalant out of an opening in dispensing valve 130 and through an aperture 140 in housing valve 100, which aperture 140 sits in concavity 145 in housing valve 100. The inhalant then travels through first end 30 and second end 50 in the nasal adaptor 10. In actual use, second end 50 would be placed in a nostril and the inhalant would travel into the nostril, through the airways to the lungs, depositing the inhalant throughout.

Figure 28:
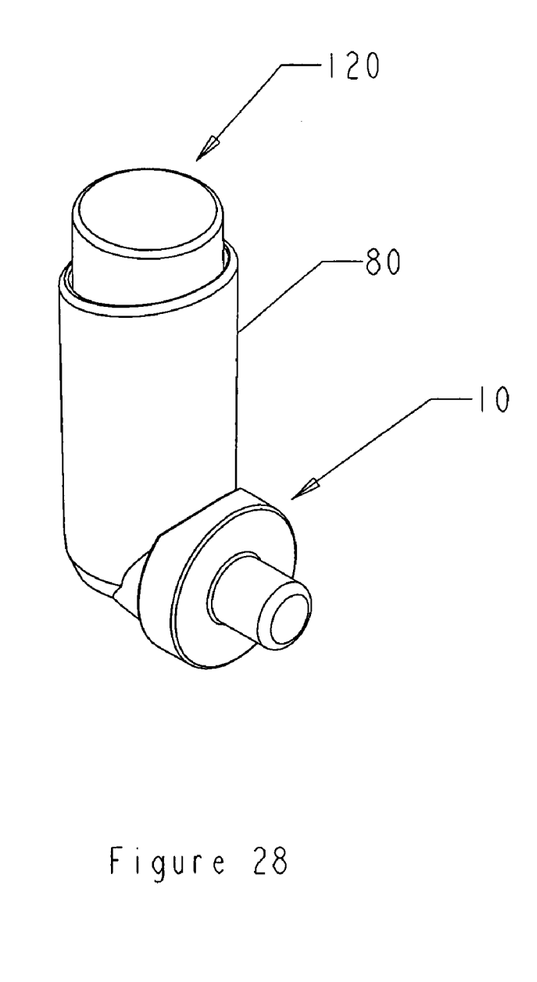
FIG. 28 is a perspective view of a modified oral metered dose inhaler device and nasal adaptor of embodiment 7, in assembly.

FIG. 28 is a perspective view of a modified oral metered dose inhaler device and nasal adaptor of embodiment 7, in assembly.

The nasal adaptors of embodiments 1, 4 and 5 found in FIGS. 1 through 4, 13 through 22 prevent medication and propellant escaping the housing and being deposited on the face or in the eyes of the patient, or just simply dissipating. The other nasal adaptors could also be modified to prevent this problem, either through modification of the nasal adaptor itself or the addition of a cap or other cover to shield the face and eyes.

The nasal adaptors may be comprised of any substance that will provide a passage for an inhalant and is safe for insertion in the nostril, such as plastics and polypropylene. The nasal adaptor may be rigid or flexible or a combination to provide extra comfort when inserted into the nostril.

Caps can also be added to the inhaler just as are provided with present inhalers which include a cover for the open end of the lower arm of the housing. Such caps may be secured to the housing for convenience and to avoid loss of the cap. Such caps may be adapted so that they fit on the lower arm of the housing with and without the nasal adaptor.

The present invention includes a kit comprising the canister containing the inhalant for delivery, housing, nasal adaptor and optionally a cap. Accordingly, the nasal adaptor may be discarded from the kit if the desired delivery is oral, or fitted onto the housing if the desired delivery is nasal. In addition, a kit may also include a housing and nasal adaptor or may include a nasal adaptor and canister.

While the above description represents the preferred embodiments of the present invention, it will be obvious that a variety of configurations not illustrated herein might well be implemented without departing from the scope of the invention or fair meaning of the accompanying claims. This includes the adaptation of nasal adaptors to fit varying designs of oral metered dose aerosol inhalers.

The invention claimed is:

1. A nasal adaptor for an oral inhaler device, which nasal adaptor has a first end and a second end, wherein said first end and said second end are the ends of a tube, and said first end has a circumference that is the same as or greater than said second end, such that when said nasal adaptor is assembled with an oral inhaler device said second end is available for insertion in a nostril, wherein said oral inhaler device further comprises a housing and a canister containing inhalant, said housing comprising an upper arm and a lower arm, and when assembled said first end is positioned within the lower arm of said housing, and wherein longitudinal flanges run between said first end and said second end to provide a snug fit when assembled, and said longitudinal flanges do not interfere with the insertion of said second end in a nostril.

2. The nasal adaptor of claim 1, wherein the longitudinal flanges include protuberances that abut the open end of said lower arm of said housing when assembled.

3. The nasal adaptor of claim 1, wherein said nasal adaptor has a circular flange at substantially the first end of said nasal adaptor.

4. A nasal adaptor for an oral inhaler device, which nasal adaptor has a first end and a second end, wherein said first end and second end are the ends of a tube, and said first end has a circumference that is the same as or greater than said second end and said second end has a circumference capable of insertion in a nostril, wherein longitudinal flanges run between said first end and said second end and said longitudinal flanges do not interfere with the insertion of said second end in a nostril.

5. The nasal adaptor of claim 4 wherein the longitudinal flanges include protuberances on the flange end closest to the second end.

6. A nasal adaptor of claim 1, wherein said second end has a circumference capable of insertion in a nostril.

7. The method of assembling the nasal adaptor of claim 4 with an oral inhaler device comprised of a housing and canister containing inhalant, said housing having an upper arm and a lower arm, by inserting the first end of said nasal adaptor into the lower arm of said housing such that said second end is available for insertion in a nostril.

8. A kit comprised of the nasal adaptor of claim 1 and an oral inhaler device.

9. A kit comprised of the nasal adaptor of claim 1 and a canister containing inhalant.

10. A kit according to claim 9 comprising a housing for holding the canister containing inhalant.

11. The nasal adaptor of claim 1, wherein the first end is sized to snugly fit to a lower arm of a housing of the oral inhaler device, the lower arm having a circumference sized for oral inhalation.

12. The nasal adaptor of claim 4, wherein the first end is sized to snugly fit to a lower arm of a housing of the oral inhaler device, the lower arm having a circumference sized for oral inhalation.

13. The method of claim of claim 7, wherein the lower arm has a circumference sized for oral inhalation.

14. The kit of claim 8, wherein the first end is sized to snugly fit to a lower arm of a housing of the oral inhaler device, the lower arm having a circumference sized for oral inhalation.

* * * * *